United States Patent [19]

Chodnekar et al.

[11] 3,957,763

[45] May 18, 1976

[54] PHENYL DERIVATIVES

[75] Inventors: Madhukar Subraya Chodnekar, Seltisberg; Ulrich Schwieter, Reinach; Peter Loeliger, Pfaffhausen; Albert Pfiffner, Bulach; Milos Suchy; Rene Zurfluh, both of Pfaffhausen, all of Switzerland

[73] Assignee: Hoffmann-La Roche Inc., Nutley, N.J.

[22] Filed: Mar. 6, 1975

[21] Appl. No.: 556,060

[30] Foreign Application Priority Data
Mar. 12, 1974 Switzerland.......................... 3416/74

[52] U.S. Cl.......................... 260/240 R; 260/345.2; 260/345.5; 260/348 R; 424/283
[51] Int. Cl.²......................................... C07D 311/02

[58] Field of Search..................... 260/345.2, 240 R

[56] References Cited
UNITED STATES PATENTS
3,671,558   6/1972   Siddall et al. ................... 260/345.7
FOREIGN PATENTS OR APPLICATIONS
2,313,505   8/1973   Germany ........................... 260/346

Primary Examiner—James O. Thomas, Jr.
Assistant Examiner—G. Breitenstein
Attorney, Agent, or Firm—Samuel L. Welt; Bernard S. Leon; Richard A. Gaither

[57] ABSTRACT

The present invention relates to phenyl derivatives, useful as insect hormones and with a method of providing a locus free of pests when using said phenyl derivatives or compositions containing same.

16 Claims, No Drawings

PHENYL DERIVATIVES

BRIEF SUMMARY OF THE INVENTION

The phenyl derivatives provided by the present invention have the following formula:

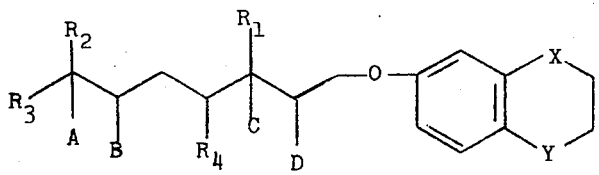

I wherein $R_1$, $R_2$ and $R_3$ are each alkyl groups containing 1 to 4 carbon atoms, $R_4$ is hydrogen or an alkyl group containing 1 to 4 carbon atoms, A and B may be taken together to form an additional bond or an oxygen bridge, C and D are each hydrogen or may be taken together to form an additional bond; X is oxygen and Y is a methylene group or Y is oxygen and X is a methylene group.

According to the process provided by the present invention, the phenyl derivatives of formula I are manufactured by:

a. reacting a compound of the formula:

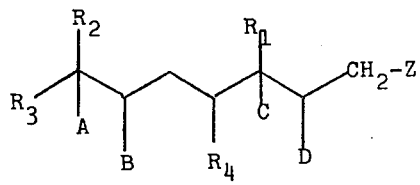

II wherein $R_1$, $R_2$, $R_3$, $R_4$, A, B, C and D are as defined above and Z is chlorine, bromine or iodine or a tosyloxy or mesyloxy group;
with a compound of the formula:

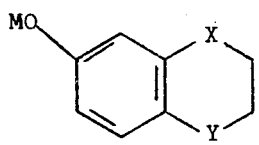

III wherein M is an alkali or alkaline earth metal and X and Y are as defined above,
or
b. hydrogenating a phenyl derivative of formula I in which C and D taken together form an additional bond, or
c. epoxidizing a phenyl derivative of formula I in which A and B taken together form an additional bond.

DETAILED DESCRIPTION OF THE INVENTION

The term "lower alkyl group containing 1 to 4 carbon atoms", as used herein, embraces methyl, ethyl, propyl, isopropyl, butyl isobutyl, sec.butyl and tert.butyl.

The instant invention is drawn to certain phenyl ether derivatives having ultimate utility as active ingredients in pesticidal compositions.

Preferred phenyl derivatives of formula I are those in which A and B taken together form an oxygen bridge and C and D taken together form an additional bond. Especially preferred are phenyl derivatives of formula I in which C and D are each hydrogen and A and B taken together form an oxygen bridge. More especially preferred are phenyl derivatives of formula I in which X represents an oxygen atom and Y represents a methylene group.

Particularly preferred phenyl derivatives of formula I are:

7-(6,7-epoxy-3,4,7-trimethyl-2-octenyloxy)-chromane,
7-(6,7-epoxy-3,7-dimethyl-2-octenyloxy)-chromane,
7-(6,7-epoxy-3,7-dimethyl-octyloxy)-chromane,
7-(6,7-epoxy-3,7-dimethyl2-nonenyloxy)-chromane,
7-(6,7-epoxy-3,7-dimethyl-nonyloxy)-chromane,
7-(6,7-epoxy-3-ethyl-7-methyl-2-nonenyloxy)-chromane,
7-(6,7-epoxy-3-ethyl-7-methyl-nonyloxy)-chromane,
7-(6,7-epoxy-3-methyl-7-ethyl-2-nonenyloxy)-chromane,
7-(6,7-epoxy-3-methyl-7-ethyl-nonyloxy)-chromane,
7-(6,7-epoxy-3,7,9-trimethyl-2-decenyloxy)-chromane,
7-(6,7-epoxy-3,7,9-trimethyl-decyloxy)-chromane,
7-(6,7-epoxy-3-ethyl-4,7-dimethyl-2-octenyloxy)-chromane,
7-(6,7-epoxy-3-ethyl-4,7-dimethyl-2-nonenyloxy)-chromane,
7-(6,7-epoxy-3-ethyl-4,7-dimethyl-nonyloxy)-chromane, and
7-(6,7-epoxy-3,4,7-trimethyl-octyloxy)-chromane.

Preferred starting materials corresponding to formula II are:

1-bromo-3,7-dimethyl-2,6-octadiene,
1-bromo-3,7-dimethyl-2,6-nonadiene,
1-bromo-3-ethyl-7-methyl-2,6-nonadiene,
1-bromo-3-methyl-7-ethyl-2,6-nonadiene,
1-bromo-3,7-diethyl-2,6-nonadiene,
1-bromo-3,7,9-trimethyl-2,6-decadiene,
1-bromo-3-ethyl-4,7-dimethyl-2,6-octadiene, and
1-bromo-3-ethyl-4,7-dimethyl-2,6-nonadiene.

The reaction of a phenolate of formula III with a halide, tosylate or mesylate of formula II is carried out in an inert organic solvent selected from the group consisting of ether, amides, and acetals, preferably in dimethylformamide, dioxane, hexamethylphosphoric acid triamide, tetrahydrofuran, dimethoxyethane, either singly or in admixture. It is expedient to carry out the reaction using the phenol corresponding to the compound of formula II in the presence of an alkali metal or alkaline earth metal, preferably sodium, or a corresponding hydride or amide, preferably sodium hydride or sodium amide. By this means, the corresponding phenolate is formed from the phenol. Preferred alkali metals are sodium and potassium and preferred alkaline earth metals are calcium and magnesium. The temperature at which the reaction is carried out is not a critical feature of the invention. The reaction can conveniently be carried out at a temperature from between about −20°C. and the boiling point of the reaction mixture. It is preferred to carry out the reaction at room temperature, when Z in formula II is bromine.

Phenyl derivatives of formula I in which C and D taken together form an additional bond may be hydrogenated with catalytically activated hydrogen in an inert organic solvent, e.g., ethyl acetate or methanol at a temperature between room temperature and the boiling point of the solvent and under normal or elevated pressure. Suitable catalysts are, for example, Raney nickel and noble metals such as platinum and palladium.

The epoxidation of a phenyl derivative of formula I, in which A and B taken together are an additional bond, may be conveniently carried out by dissolving said phenyl derivative in an inert solvent, such as methylene chloride or chloroform, and treating the solution with an organic peracid, e.g., peracetic acid, perbenzoic acid, m-chloroperbenzoic acid or perphthalic acid or by suspending said phenyl derivative in water, treating the suspension with a sufficient quantity of an inert solvent, e.g., dioxane, tetrahydrofuran or 1,2-dimethoxyethane to provide a homogeneous concentrated solution and introducing N-bromosuccinimide portionwise into this solution. Either procedure may be conducted at a temperature between 0°C. and room temperature. The resulting bromohydrin can be smoothly converted into the desired epoxide by the action of alkalis, especially sodium methylate in methanol.

Certain of the starting materials of formula II are novel. They can be prepared, for example, by reacting a compound of formula IV hereinafter with acethylene in the presence of sodium amide in liquid ammonia and partially hydrogenating the resulting triply unsaturated compound using a partially deactivated catalyst, e.g., a lead/palladium catalyst deactivated with quinoline. The resulting alcohol of formula Va is halogenated under allylic rearrangement in a known manner. As the halogenating agent, there is preferably used a phosphorus halide, especially phosphorus tribromide. The halogenating agent is allowed to act on the alcohol in the cold, advantageously at a temperature between −10°C. and +5°C. Further, a compound of formula IV can be reacted in a known manner by means of a Horner reaction to give a compound of formula V,b. The further procedure to give the compounds of formulae VI, b and VI,c shown in the following sample scheme is also known per se. In this formula scheme, $R_1$, $R_2$, $R_3$ and $R_4$ have the significance given earlier:

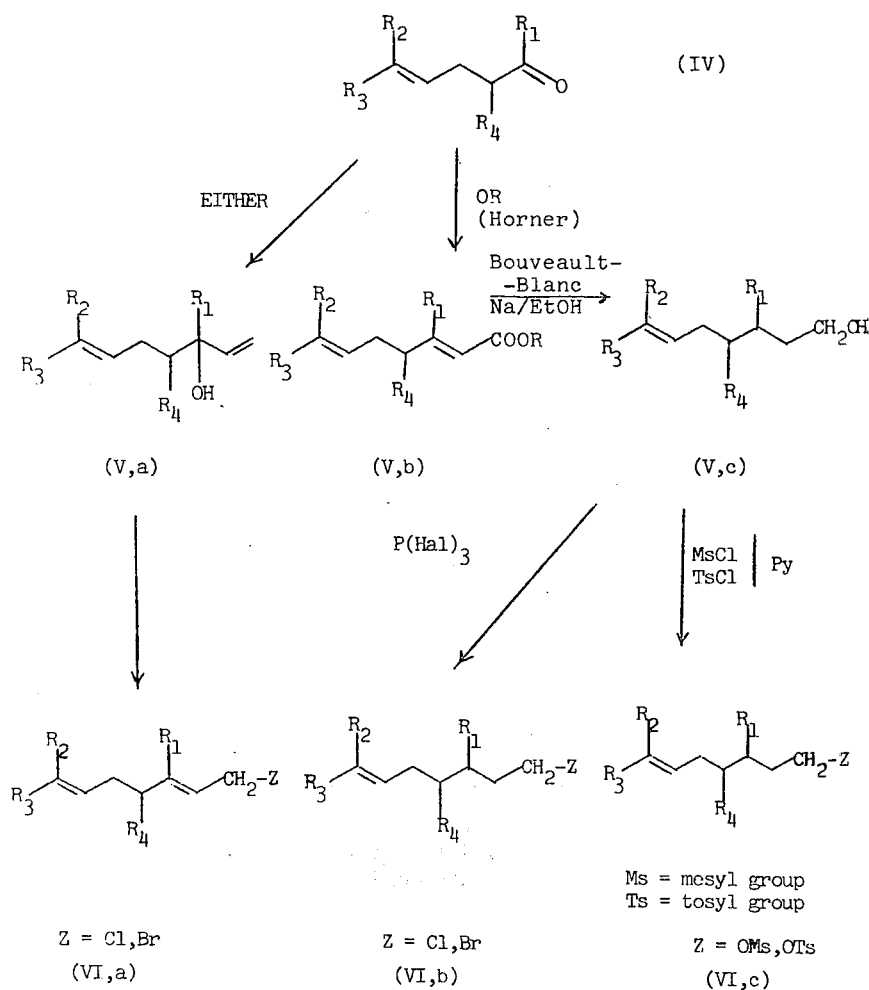

The compounds of formula IV can be obtained, for example, according to the "Saucy-Marbet" method [Helv., 50, 2091-2100, (1967)] or according to "Marc Julia" synthesis [Bull. Soc. Chem. France, 1072 (1960)]. This preparation is illustrated in the following formula scheme in which $R_1$, $R_2$, $R_3$ and $R_4$ are as previously defined.

practically non-poisonous to vertebrates. The toxicity of the phenyl derivatives of formula I lies at over 1000 mg/kg body weight. Moreover, the present phenyl derivatives are readily degraded. The danger of a cumulation is therefore excluded. The phenyl derivatives of formula I can accordingly be used for controlling pests in connection with animals, plants and foodstuffs.

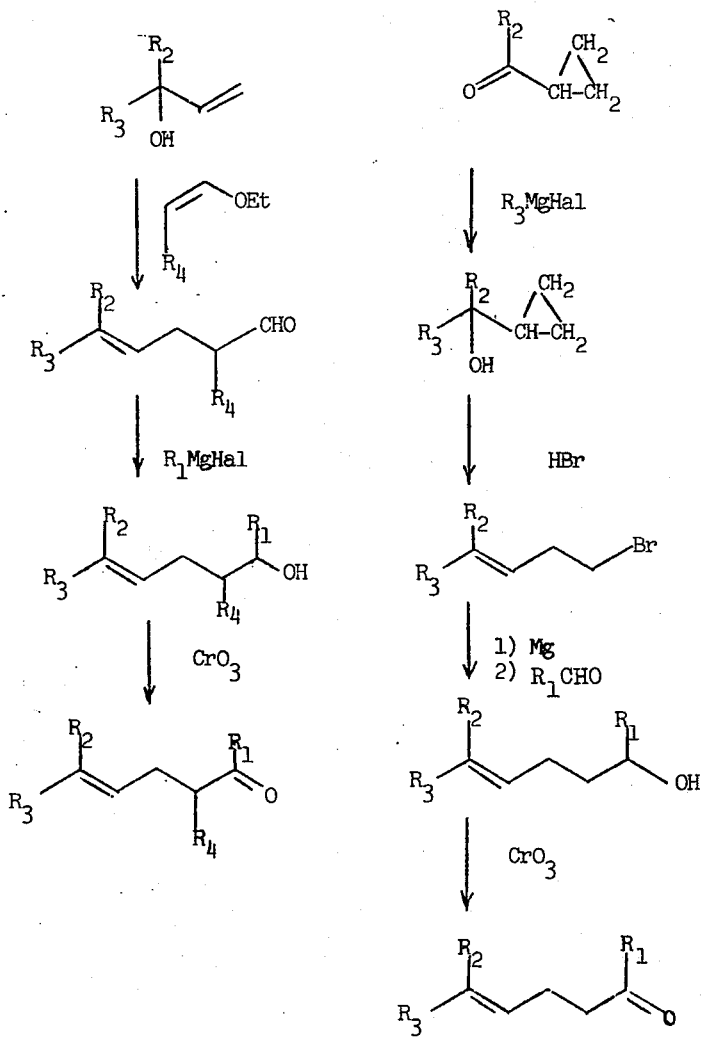

The conditions for the individual steps of the foregoing formula scheme are generally known.

Due to the fact that the side-chain is unsaturated, the phenyl derivatives of formula I occur as cis/trans isomer mixtures. The isomer mixture can be separated into the individual isomers in the usual manner, for example, by fractional distillation or preparative gas chromatography. Further, isomeric starting materials of formula II can also be separated into the individual isomers by fractional distillation or chromatography.

The phenyl derivatives of formula I are suitable for the control of pests. In contrast to most of the hitherto known pesticides, which kill, cripple or drive away the pests as contact- or feed-poisons, the phenyl derivatives of formula I interfere with the hormonal system of the animal organism. In insects, for example, the metamorphosis to the imago, the laying of viable eggs and the development of laid normal eggs are disturbed. The sequence of generations is interrupted and the insects are indirectly killed. The present phenyl derivatives are The phenyl derivatives of formula I are especially suitable for the control of invertebrates, preferably Arthropoda and Nematoda, especially Acarina, Orthoptera, Blattidae, Psocoids, Thysanopteroids, Hemiptera, Hymenopera, Choleoptera, Diptera, Lepidoptera and Neuroptera. Examples of such invertebrates are:

| | |
|---|---|
| Adoxophyes | |
| Epilachna | |
| Spodoptera | |
| Metatetranychus | (red citrus spider mite) |
| Tetranychus spp. | (common spider mite) |
| Anthonomus grandis | (boll weevil) |
| Chilo suppressalis | (Asiatic rice borer) |
| Diatraea saccharalis | |
| Heliothia spp. | (bollworm) |
| Pyrausta nubilalis | (corn borer) |
| Carpocapsa pomonella | (codlin moth) |
| Ceratitis capitata | (Mediterranean fruit fly) |
| Aonidiella aurantii | (red Californian scale louse) |
| Aphis gossypii | (cotton aphid) |
| Myzus persicae | (peach aphid) |

| | |
|---|---|
| Locusta migratoria | (migratory locust) |
| Tribolium spp. | (rice flour beetle) |
| Sitophilus spp. | (grain weevil) |
| Ephestia kuhniella | (flour moth) |
| Plodia interpunctella | (dried fruit moth) |
| Aedes spp. | (mosquitoes) |
| Anopheles spp. | (malarial mosquito) |
| Musca domestica | (housefly) |
| Stomoxys calcitrans | (stablefly [calf-biter]) |
| Blattella germanica | (cockroach) |
| Cochliomyia hominivorax | (screw worm) |
| Tribolium castaneum | |
| Leptinotarsa | |

The phenyl derivatives of formula I are especially suitable for the control of flies and mosquitos, especially for Diptera such as Culicidae.

As will be seen from the following, a concentration of $10^{-3}$ to $10^{-6}$ g/cm² of a phenyl derivative of formula I is generally sufficient to insure the desired effect.

The phenyl derivatives of formula I can be used as pesticides in the form of concentrates or granulates or, together with carriers, in the form of sprays, aerosols or powders. For certain purposes, it may be advantageous to use emulsions, suspensions or solutions which contain emulsifiers or wetting agents. Examples of solid carrier materials which may be used are chalk, talc, bentonite, kaolin, diatomaceous earth, siliceous earth, fuller's earth, lime, gypsum, powders and dusts from organic waste products etc.

In general, the pesticidal compositions provided by the present invention can be formulated according to procedures which are described, for example, in Farm Chemicals, Volume 128, page 52 et seq. The pesticidal compositions can also contain other additives such as emulsifiers or masking agents.

The pesticidal composition can be made up in the form of concentrates which are suitable for storage and transport. Such concentrates can contain, for example, 40–90% of a phenyl derivative of formula I. These concentrates can be diluted with the same or different carrier materials to provide concentrations which are suitable for practical use. In the ready-for-use pesticidal composition suitable for spraying, a phenyl derivative of formula I can be present, for example, in a concentration of 0.01–0.5%, preferably 0.1%. The concentration can, however, also be larger or smaller.

The phenyl derivatives of formula I in emulsified form are as stable in water as known compounds with the same type of action.

The pesticidal compositions provided by this invention can be used against pests according to the usual methods; for example by contact or by intake with food.

It will accordingly be appreciated that this invention includes within its scope (a) a pesticidal composition which contains as an essential active ingredient or essential active ingredients one or more of the phenyl derivatives of formula I hereinbefore in association with a compatible carrier material and (b) a method of rendering a locus subject to or subjected to attack by pests free from such attack by applying to said locus a pesticidal composition as hereinbefore defined or one or more of the aforesaid phenyl derivatives.

The following non-limiting examples illustrate the process provided by the present invention.

EXAMPLE 1

While stirring and flushing with nitrogen, 79.3 g. of 7-hydroxy-chromane in 320 ml. of dimethylformamide are added dropwise at room temperature to 37.3 g. of powdered technical potassium hydroxide in 138 ml. of dimethylformamide and stirred for 1 hour. While cooling with ice, 151.4 g. of 1-bromo-3,7-dimethyl-2,6-nonadiene are added dropwise at 0°–10°C. and the mixture is stirred for an additional 20 hours at room temperature. The mixture is poured on to 1200 ml. of water and extracted three times with 500 ml. of hexane. The combined hexane phases are washed twice with 600 ml. of 2-N sodium hydroxide solution and subsequently with water, dried over sodium sulphate, evaporated and distilled. There is obtained pure 7-(3,7-dimethyl-2,6-nonadienyloxy)-chromane of boiling point 148°–152°C/0.001 mmHg; $n_D^{20} = 1.5376$.

EXAMPLE 2

Following the procedure of Example 1, 1-bromo-3,4,7-trimethyl-2,6-octadiene and 7-hydroxy-chromane are reacted to form 7-(3,4,7-trimethyl-2,6-octadienyloxy)-chromane; $n_D^{20} = 1.5368$.

EXAMPLE 3

Following the procedure of Example 1, 1-bromo-3,7-dimethyl-2,6-octadiene and 7-hydroxy-chromane are reacted to form 7-(3,7-dimethyl-2,6-octadienyloxy)-chromane; $n_D^{20} = 1.5359$.

EXAMPLE 4

Following the procedure of Example 1, 1-bromo-3-ethyl-7-methyl-2,6-nonadiene and 7-hydroxy-chromane are reacted to form 7-(3-ethyl-7-methyl-2,6-nonadienyloxy)-chromane of boiling point 140°–141°C/0.001 mmHg.

EXAMPLE 5

Following the procedure of Example 1, 1-bromo-3-methyl-7-ethyl-2,6-nonadiene and 7-hydroxy-chromane are reacted to form 7-(3-methyl-7-ethyl-2,6-nonadienyloxy)-chromane, $n_D^{20} = 1.5342$.

EXAMPLE 6

Following the procedure of Example 1, 1-bromo-3,7,9-trimethyl-2,6-decadiene and 7-hydroxy-chromane are reacted to form 7-(3,7,9-trimethyl-2,6-decadienyloxy)-chromane, $n_D^{20} = 1.5920$.

EXAMPLE 7

Following the procedure of Example 1, 1-bromo-3-ethyl-4,7-dimethyl-2,6-octadiene and 7-hydroxy-chromane are reacted to form 7-(3-ethyl-4,7-dimethyl-2,6-octadienyloxy)-chromane, $n_D^{20} = 1.5286$.

EXAMPLE 8

Following the procedure of Example 1, 1-bromo-3-ethyl-4,7-dimethyl-2,6-nonadiene and 7-hydroxy-chromane are reacted to form 7-(3-ethyl-4,7-dimethyl-2,6-nonadienyloxy)-chromane, $n_D^{20} = 1.5226$.

The following examples illustrate the preparation of starting materials corresponding to compounds of formula II.

EXAMPLE 9

36 ml. of pyridine are added to 252 g. of ethyl-linalool in 428 ml. of pentane, treated at −7°C. for 2 hours with a solution of 181.5 g. of phosphorus tribromide and stirred for an additional 30 minutes at 0°C. The reaction mixture is worked up by pouring the solution on to ice, stirring for 30 minutes and diluting with 500 ml. of pentane. The pentane layer is separated, washed with saturated sodium bicarbonate solution and saturated sodium chloride solution, dried over sodium sulphate and evaporated. There are obtained 340 g. of 1-bromo-3,7-dimethyl-2,6-nonadiene which is used without further purification for reaction with 7-hydroxy-chromane.

EXAMPLE 10

Following the procedure of Example 9, 4-methyl-linalool and phosphorus tribromide are reacted to form 1-bromo-3,4,7-trimethyl-2,6-octadiene.

EXAMPLE 11

Following the procedure of Example 9, linalool and phosphorus tribromide are reacted to form 1-bromo-3,7-dimethyl-2,6-octadiene.

EXAMPLE 12

Following the procedure of Example 9, 3-ethyl-7-methyl-1,6-nonadien-3-ol and phosphorus tribromide are reacted to form 1-bromo-3-ethyl-7-methyl-2,6-nonadiene.

EXAMPLE 13

Following the procedure of Example 9, 3-methyl-7-ethyl-1,6-nonadien-3-ol and phosphorus tribromide are reacted to form 1-bromo-3-methyl-7-ethyl-2,6-nonadiene.

EXAMPLE 14

Following the procedure of Example 9, 3,7,9-trimethyl-1,6-decadien-3-ol and phosphorus tribromide are reacted to form 1-bromo-3,7,9-trimethyl-2,6-decadiene.

EXAMPLE 15

Following the procedure of Example 9, 3-ethyl-4,7-dimethyl-1,6-octadien-3-ol and phosphorus tribromide are reacted to form 1-bromo-3-ethyl-4,7-dimethyl-2,6-octadiene.

EXAMPLE 16

Following the procedure of Example 9, 3-ethyl-4,7-dimethyl-1,6-nonadien-3-ol and phosphorus tribromide are reacted to form 1-bromo-3-ethyl-4,7-dimethyl-2,6-nonadiene.

As with Example 9, all of the 1-bromo compounds were used without further purification in reactions with 7-hydroxy-chromane.

EXAMPLE 17

A mixture of 118.8 g. of 7-(3,7-dimethyl-2,6-nonadienyloxy)-chromane, 26 g. of anhydrous sodium acetate in 910 ml. of chloroform is treated over a period of 1 hour with 80 g. of 40% peracetic acid while stirring and flushing with nitrogen at 0°–2°C. The resulting mixture is subsequently stirred for an additional 15 minutes. The mixture is washed successively with a saturated sodium chloride solution, 10% sodium bicarbonate 0.1-N sodium thiosulphate solution and water, dried over sodium sulphate and concentrated. By filtration over 600 g. of silica gel with hexane/ether (9:1) and subsequent molecular distillation, there is obtained 7-(6,7-epoxy-3,7-dimethyl-2-nonenyloxy)-chromane, $n_D^{20} = 1.5295$.

EXAMPLE 18

Following the procedure of Example 17, 7-(3,4,7-trimethyl-2,6-octadienyloxy)-chromane and peracetic acid are reacted to form 7-(6,7-epoxy-3,4,7-trimethyl-2-octenyloxy)-chromane, $n_D^{20} = 1.5311$.

EXAMPLE 19

Following the procedure of Example 17, 7-(3,7-dimethyl-2,6-octadienyloxy)-chromane and peracetic acid are reacted to form 7-(6,7-epoxy-3,7-dimethyl-2-octenyloxy)-chromane, $n_D^{20} = 1.5341$.

EXAMPLE 20

Following the procedure of Example 17, 7-(3-ethyl-7-methyl-2,6-nonadienyloxy)-chromane and peracetic acid are reacted to form 7-(6,7-epoxy-3-ethyl-7-methyl-2-nonenyloxy)-chromane, $n_D^{20} = 1.5292$.

EXAMPLE 21

Following the procedure of Example 17, 7-(3-methyl-7-ethyl-2,6-nonadienyloxy)-chromane and peracetic acid are reacted to form 7-(6,7-epoxy-3-methyl-7-ethyl-2-nonenyloxy)-chromane, $n_D^{20} = 1.5303$.

EXAMPLE 22

Following the procedure of Example 17, 7-(3,7,9-trimethyl-2,6-decadienyloxy)-chromane and peracetic acid are reacted to form 7-(6,7-epoxy-3,7,9-trimethyl-2-decenyloxy)-chromane, $n_D^{20} = 1.5256$.

EXAMPLE 23

Following the procedure of Example 17, 7-(3-ethyl-4,7-dimethyl-2,6-octadienyloxy)-chromane and peracetic acid are reacted to form 7-(6,7-epoxy-3-ethyl-4,7-dimethyl-2-octenyloxy)-chromane, $n_D^{20} = 1.5287$.

EXAMPLE 24

Following the procedure of Example 17, 7-(3-ethyl-4,7-dimethyl-2,6-nonadienyloxy)-chromane and peracetic acid are reacted to form 7-(6,7-epoxy-3-ethyl-4,7-dimethyl-2-nonenyloxy)-chromane, $n_D^{20} = 1.5190$.

EXAMPLE 25

2.6 g. of 7-(6,7-epoxy-3,7-dimethyl-2-nonenyloxy)-chromane are dissolved in 26 ml. of ethyl acetate and hydrogenated in the presence of 130 mg. of platinum oxide until the theoretical amount of hydrogen has been made up. The mixture is then filtered off from the catalyst, evaporated and chromatographed on silica gel with hexane/ether (7:3). There is obtained pure 7-(6,7-epoxy-3,7-dimethyl-nonyloxy)-chromane, $n_D^{20} = 1.5159$.

EXAMPLE 26

Following the procedure of Example 25, 7-(6,7-epoxy-3,7-dimethyl-2-octenyloxy)-chromane is hydrogenated to form 7-(6,7-epoxy-3,7-dimethyl-octyloxy)-chromane, $n_D^{20} = 1.5170$.

EXAMPLE 27

Following the procedure of Example 25, 7-(6,7-epoxy-3-ethyl-7-methyl-2-nonenyloxy)-chromane is hydrogenated to form 7-(6,7-epoxy-3-ethyl-7-methyl-nonyloxy)-chromane, $n_D^{20} = 1.5159$.

EXAMPLE 28

Following the procedure of Example 25, 7-(6,7-epoxy-3-methyl-7-ethyl-2-nonenyloxy)-chromane is hydrogenated to form 7-(6,7-epoxy-3-methyl-7-ethyl-nonyloxy)-chromane, $n_D^{20} = 1.5149$.

EXAMPLE 29

Following the procedure of Example 25, 7-(6,7-epoxy-3,7,9-trimethyl-2-decenyloxy)-chromane is hydrogenated to form 7-(6,7-epoxy-3,7,9-trimethyl-decyloxy)-chromane, $n_D^{20} = 1.5110$.

EXAMPLE 30

Following the procedure of Example 25, 7-(6,7-epoxy-3-ethyl-4,7-dimethyl-2-nonenyloxy)-chromane is hydrogenated to form 7-(6,7-epoxy-3-ethyl-4,7-dimethyl-nonyloxy)-chromane, $n_D^{20} = 1.5133$.

EXAMPLE 31

Following the procedure of Example 25, 7-(6,7-epoxy-3,4,7-trimethyl-2-octenyloxy)-chromane is hydrogenated to form 7-(6,7-epoxy-3,4,7-trimethyl-octyloxy)-chromane, $n_D^{20} = 1.5191$.

The following example illustrates a pesticidal compositon containing a typical phenyl derivative provided by this invention.

EXAMPLE 32

500 g. of 7-(6,7-epoxy-3,7-dimethyl-2-nonenyloxy)-chromane are mixed with 100 g. of a mixture of a condensation product of an alkyl phenol and ethylene oxide and a salt of an alkyl-arylsulphonic acid (Atlox 2081B)*. The mixture is made up to 1000 ml. with tri(n-alkyl)-benzenes (aromatic content 99.5%; boiling range 187°–213°C.)**. The concentrate is brought to the desired dilution with water before use and is sprayed on to the locus to be protected.

*Atlas Chemie,Essen (Germany)
** Shell Sol AB (Shell, Switzerland)

We claim:
1. Phenyl derivatives of the formula:

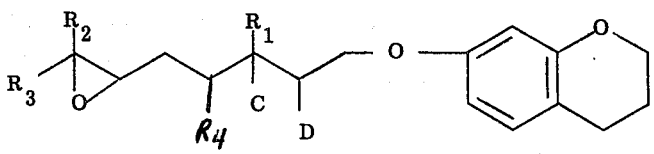

wherein $R_1$, $R_2$ and $R_3$ are each alkyl groups containing 1 to 4 carbon atoms, $R_4$ is a hydrogen atom or an alkyl group containing 1 to 4 carbon atoms, and C and D are each hydrogen or may be taken together to form an additional bond.

2. The phenyl derivatives of claim 1 having the formula:

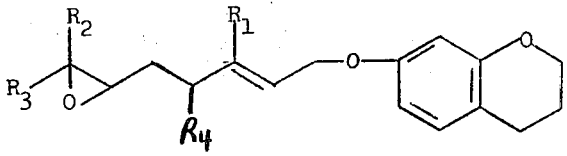

wherein $R_1$, $R_2$, $R_3$ and $R_4$ are as defined in claim 3.

3. The phenyl derivatives of claim 1 having the formula:

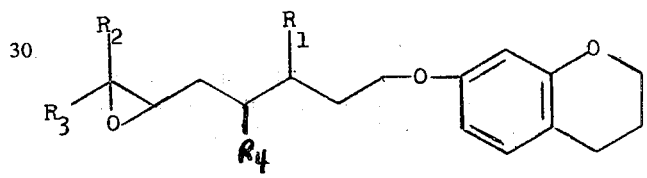

wherein $R_1$, $R_2$, $R_3$ and $R_4$ are as defined in claim 3.

4. The phenyl derivative of claim 2 wherein said derivative is 7-(6,7-epoxy-3-ethyl-4,7-dimethyl-2-octenyloxy)-chromane.

5. The phenyl derivative of claim 3 wherein said derivative is 7-(6,7-epoxy-3-ethyl-4,7-dimethyl-nonyloxy)-chromane.

6. The phenyl derivative of claim 3 wherein said derivative is 7-(6,7-epoxy-3,4,7-trimethyl-octyloxy)-chromane.

7. The phenyl derivative of claim 2 wherein said derivative is 7-(6,7-epoxy-3,7-dimethyl-2-octenyloxy)-chromane.

8. The phenyl derivative of claim 2 wherein said derivative is 7-(6,7-epoxy-3,7-dimethyl-2-nonenyloxy)-chromane.

9. The phenyl derivative of claim 2 wherein said derivative is 7-(6,7-epoxy-3-ethyl-7-methyl-2-nonenyloxy)-chromane.

10. The phenyl derivative of claim 2 wherein said derivative is 7-(6,7-epoxy-3-methyl-7-ethyl-2-nonenyloxy)-chromane.

11. The phenyl derivative of claim 2 wherein said derivative is 7-(6,7-epoxy-3,7,9-trimethyl-2-decenyloxy)-chromane.

12. The phenyl derivative of claim 3 wherein said derivative is 7-(6,7-epoxy-3,7-dimethyl-octyloxy)-chromane.

13. The phenyl derivative of claim 3 wherein said derivative is 7-(6,7-epoxy-3,7-dimethyl-nonyloxy)-chromane.

14. The phenyl derivative of claim 3 wherein said derivative is 7-(6,7-epoxy-3-ethyl-7-methyl-nonyloxy)-chromane.

15. The phenyl derivative of claim 3 wherein said derivative is 7-(6,7-epoxy-3-methyl-7-ethyl-nonyloxy)-chromane.

16. The phenyl derivative of claim 3 wherein said derivative is 7-(6,7-epoxy-3,7,9-trimethyl-decyloxy)-chromane.

* * * * *